United States Patent [19]

Hermes et al.

[11] Patent Number: 5,312,437
[45] Date of Patent: May 17, 1994

[54] ABSORBABLE COATING COMPOSITION AND SUTURE COATED THEREWITH

[75] Inventors: Matthew E. Hermes, Easton; Donald S. Kaplan, Weston; Nagabhushanam Totakura, Norwalk; Steven L. Bennett, Milford, all of Conn.

[73] Assignee: United States Surgical Corporation, Norwalk, Conn.

[21] Appl. No.: 896,856

[22] Filed: Jun. 12, 1992

[51] Int. Cl.$^5$ .............................................. A61L 17/00
[52] U.S. Cl. .................... 606/230; 606/231; 428/375; 428/378
[58] Field of Search ............... 606/230, 231; 428/275, 428/375, 378; 525/354, 408

[56] References Cited

U.S. PATENT DOCUMENTS

| | | | |
|---|---|---|---|
| 3,531,561 | 9/1970 | Trehu | 606/231 |
| 3,867,190 | 2/1975 | Schmitt et al. | 606/231 |
| 3,942,532 | 3/1976 | Hunter et al. | 606/230 |
| 4,027,676 | 6/1977 | Mattei | 606/230 |
| 4,043,344 | 8/1977 | Landi et al. | 606/230 |
| 4,047,533 | 9/1977 | Perciaccante | 606/230 |
| 4,080,969 | 3/1978 | Casey et al. | 606/231 |
| 4,105,034 | 8/1978 | Shalaby et al. | 606/230 |
| 4,185,637 | 1/1980 | Mattei | 606/230 |
| 4,201,216 | 5/1980 | Mattei | 606/230 |
| 4,470,416 | 9/1984 | Kafrawy et al. | 606/230 |
| 4,624,256 | 11/1986 | Messier et al. | 606/230 |
| 4,649,920 | 3/1987 | Rhum | 606/237 |
| 4,653,497 | 3/1987 | Bezwada et al. | 606/230 |
| 4,705,820 | 11/1987 | Wang et al. | 606/230 |
| 4,711,241 | 12/1987 | Lehmann | 606/230 |
| 4,716,203 | 12/1987 | Casey et al. | 606/230 |
| 4,744,365 | 5/1988 | Kaplan et al. | 606/230 |
| 4,788,979 | 12/1988 | Jarrett et al. | 606/230 |
| 4,857,602 | 8/1989 | Casey et al. | 606/230 |
| 5,123,912 | 6/1992 | Kaplan et al. | 606/230 |

FOREIGN PATENT DOCUMENTS 0239775  10/1987  European Pat. Off. .............. 606/77

Primary Examiner—Stephen C. Pellegrino
Assistant Examiner—Gary Jackson

[57] ABSTRACT

An absorbable composition for application to a surgical suture to improve the knot tie-down and/or knot security characteristics thereof is obtained from the reaction of a poly(oxypropylene) glycol and a lactide/glycolide copolymer, optionally, in the presence of an initiator and/or catalyst.

36 Claims, No Drawings

ABSORBABLE COATING COMPOSITION AND SUTURE COATED THEREWITH

BACKGROUND OF THE INVENTION

This invention relates to an absorbable coating composition for surgical sutures and to a coated surgical suture exhibiting improved knot tie-down and/or knot security characteristics.

Since monofilament synthetic absorbable suture materials are generally stiffer than their catgut or collagen counterparts, multifilament, e.g., braided or twisted, constructions have been employed in many instances for greater softness and flexibility. Multifilament sutures, however, exhibit a certain degree of undesirable roughness in what is generally referred to as knot tie-down performance, i.e., the ease or difficulty of sliding a knot into place down the suture. It has therefore become a common practice to coat sutures, particularly those of the multifilament variety, with compositions which improve their knot tie-down performance and perhaps one or more other properties of the sutures as well. Known suture coating compositions include those described in U.S. Pat. Nos. 3,867,190; 3,942,532; 4,027,676; 4,043,344; 4,047,533; 4,080,969; 4,105,034; 4,185,637; 4,201,216; 4,470,416; 4,624,256; 4,649,020; 4,716,203, 4,788,979; and, 4,857,602.

U.S. patent application Ser. No. 07/707,437, filed May 28, 1991 describes an absorbable composition for improving the knot tie-down properties of a suture, the composition being either a copolymer derived from the copolymerization of a low molecular weight poly(oxyethylene) glycol, glycolide monomer and a lactide monomer or a copolymer derived from the copolymerization of a low molecular weight polyalkylene glycol and a preformed copolymer of lactide and glycolide.

Notwithstanding the extensive research in attempting to improve the tie-down characteristics of surgical sutures, sutures having even further improved knot tie-down properties are still desirable.

SUMMARY OF THE INVENTION

It is an object of the present invention to provide an absorbable coating composition for surgical sutures, particularly multifilament synthetic sutures.

Another object of this invention is to provide a coated surgical suture exhibiting improved knot tie-down characteristics.

Still another object of the present invention is to provide an absorbable coated synthetic suture exhibiting improved knot tie-down characteristics under both wet and dry conditions.

A further object of this invention is to provide an absorbable coated synthetic suture exhibiting improved knot security characteristics.

These and other objects are achieved herein by providing an absorbable coating composition comprising the product obtained by reacting a mixture of poly(oxypropylene) glycol and a lactide/glycolide copolymer in the presence or absence of an initiator. Coated sutures having improved knot tie-down characteristics under dry and wet conditions as well as improved knot security characteristics are provided by depositing a coating of the afore-described composition on the suture.

DESCRIPTION OF THE PREFERRED EMBODIMENTS

The preferred poly(oxypropylene) glycols used in preparing the suture coating composition of this invention possess molecular weights ranging from about 400 to about 6,000 and more preferably from about 1,000 to about 4,000 and viscosities of from about 70 to about 2,000 cp, preferably from about 150 to about 1,200 cp and, more preferably, from about 900 to about 1200 cp. Suitable poly(oxypropylene) glycols include those of the Pluracol (BASF-Wyandotte), Voranol (Dow), Poly G (Olin), Polylite (Reichhold), Thanol (Texaco) and Niax (Union Carbide) series.

The preferred lactide/glycolide copolymers are made from about 90 to about 65 mole percent lactide, from about 10 to about 35 mole percent glycolide and from 0 to about 5 mole percent of one or more additional monomers copolymerizable therewith such as p-dioxanone, ε-caprolactone, etc. Copolymers of this type and their preparation are known, e.g., from U.S. Pat. Nos. 2,668,162; 2,703,316; 3,297,033; 3,620,218; 3,636,956; 3,736,646; 3,773,919,; 3,797,499; 3,839,297; 3,867,190; 3,982,543; 4,273,920; and, 4,523,591.

More preferred lactide/glycolide copolymers for use in preparing the coating composition herein are the 85-70 mole percent lactide/15-30 mole percent glycolide copolymers described in U.S. Pat. No. 4,523,591, the contents of which are incorporated by reference herein. The copolymers are advantageously prepared with L-lactide and possess a glass transition temperature of at least about 54° C. when measured by differential scanning calorimetry at 20° C./min and an inherent viscosity of at least about 0.9 when measured in chloroform at a concentration of 0.25 g/dl. A particularly preferred lactide/glycolide copolymer is prepared with about 18 mole percent lactide and about 82 mole percent glycolide.

The absorbable coating composition herein is prepared by reacting the poly(oxypropylene) glycol(s) with the lactide/glycolide copolymer(s), generally in the presence of an esterification catalyst such as stannous chloride, stannous octoate, etc., and, optionally, an initiator. Suitable initiators include glycols such as ethylene glycol, propylene glycol, diethylene glycol and dipropylene glycol. A preferred glycol, diethylene glycol, is advantageously employed at a level of from about 0.01 to about 0.1 weight percent, and preferably at a level of from about 0.02 to about 0.5 weight percent, of the reaction medium. The weight ratio of poly(oxypropylene) glycol to lactide/glycolide copolymer can vary from about 4:1 to about 1:4 and preferably from about 2:1 to about 1:2, respectively. Typically, the reaction is carried out in an inert atmosphere, e.g., nitrogen, at temperatures, for example, of from about 125° to about 200° C., and preferably from about 150° to about 160° C. When employing a lactide/glycolide copolymer possessing an inherent viscosity of at least about 0.9, it is preferred to carry out the reaction until the inherent viscosity of the coating composition has fallen below about 0.9, and more preferably below about 0.5, when measured in chloroform at a concentration of 0.25 g/dl. Reaction periods of from about 10 to about 24 hours are generally sufficient to accomplish this.

The absorbable coating composition of the present invention is non-toxic and physiologically inert. It can be applied to the surface of a suture in the form of a solution and/or dispersion in a volatile carrier such as methylene chloride or acetone. Solidification of the coating on the suture surface occurs upon evaporation of the carrier.

The coating composition can be applied to a suture by any suitable process, e.g., passing the suture through a solution of the coating composition, past a brush or other coating solution applicator, or past one or more spray nozzles dispensing the coating solution. The suture wetted with the coating solution is subsequently passed through or held in a drying oven for a time and at a temperature sufficient to volatilize and drive off the solvent.

The coating composition can, if desired, contain one or more other components, e.g., dyes, antibiotics, antiseptics, growth factors, anesthetics, anti-inflammatory agents, etc.

While the coating composition herein can be applied to any type of suture, it is essentially intended for application to a braided suture, a preferred type of which is disclosed in U.S. Pat. No. 5,019,093, the contents of which are incorporated by reference herein. The amount of coating composition applied to a braided suture will vary depending upon the structure of the suture, e.g., the number of filaments, tightness of braid or twist, the size of the suture and its composition.

The coating composition herein can be used for both "unfilled" as well as "filled" sutures, the latter designating braided bioabsorbable sutures containing a storage stabilizing material as disclosed in U.S. Pat. Nos. 5,037,429 or 5,051,272, the contents of which are incorporated by reference herein. For an "unfilled" suture, the coating composition can be applied at a level of from about 0.5 to about 4 weight percent or more and preferably from about 1 to about 3 weight percent. Advantageously, the coating composition is applied to the suture prior to application of the storage stabilizing material. For a filled suture, the amount of applied coating composition can range from about 0.2 to as much as about 3 weight percent or more and preferably from about 0.5 to about 2 weight percent. As a practical matter, it is generally preferred to apply the minimum amount of coating composition consistent with good tie-down performance. This level of coating add-on can be readily determined for any particular suture coating system employing routine experimental procedures.

In the case of an unfilled or filled braided suture, prior to application of the coating composition, it can be advantageous to calender the suture in order to improve the uniformity with which the coating composition is laid down upon the suture surface. A calendering operation can also be beneficial when carried out on a coated suture where the suture is to be filled with a storage stabilizing material. In this case, calendering will tend to break up the coating facilitating penetration of the interior spaces of the suture by the storage stabilizing material.

A preferred method for calendering a braided suture and an apparatus for carrying out the method are disclosed in copending U.S. patent application Ser. No. 07/652,939, filed Feb. 8, 1991, the contents of which are incorporated by reference herein. In accordance with Ser. No. 07/652,939, calendering of a braided suture is achieved by applying a compressive force to the suture in a first line or direction generally transverse to the longitudinal direction of the suture, the compressive force being of sufficient magnitude as to flatten the suture in a direction orthogonal to the direction in which the compressive force is applied. Preferably, a second application of compressive force is applied to the suture in a direction generally transverse to that of the first compressive force and transverse to the longitudinal direction of the suture. The second compressive force is substantially equal in magnitude to the first compressive force so that the suture returns to its original cross-sectional configuration.

The apparatus for implementing the foregoing calendering method includes at least one pair of rollers which are biased towards each other to apply a compressive force to the suture as the suture passes between them. Optionally, a second pair of rollers is provided which is oriented at an angle (preferably 90°) to the first pair of rollers and transverse to the longitudinal direction of the suture. Following passage between both the first and second pair of rollers, the suture will have been alternately compressed, or flattened, in a first direction and thereafter in a second direction at an angle to the first direction.

The following examples are illustrative of the absorbable coating composition of this invention, its preparation and sutures coated therewith.

EXAMPLE 1

This example illustrates the preparation of an absorbable suture coating composition in accordance with the invention.

A poly(oxypropylene) glycol of 4,000 average molecular weight (nominal) and a viscosity of from 900–1200 cp, 677±1 g, was introduced into a reactor equipped with a stirrer. Following a minimum 6 hour period of drying the poly(oxypropylene) glycol in a stream of anhydrous nitrogen gas, a previously dried lactide/glycolide copolymer containing 82 mole percent lactide and 18 mole percent glycolide and an inherent viscosity of at least 0.9 when measured in chloroform at a concentration of 0.25 g/dl (prepared as disclosed in U.S. Pat. No. 4,523,591 referred to above), 1,323±1 g, was introduced into the reactor. The reactor, which was maintained under a blanket of nitrogen gas, was heated to a temperature of 155°–170° C. Thereafter, 0.4±0.05 g stannous octoate catalyst and 0.4±0.05 g diethylene glycol initiator were added to the reactor, the latter being stirred at a rate of 55–60 rpm. Following a reaction period of 20–25 hours, the reaction product was recovered and residual reactant(s) removed therefrom at elevated temperature and under a pressure not exceeding 10 Torr, the temperature profile being as follows:

1. Ramped to 80° C. at 5° C./hr.
2. Soaked at 80° C. for 1 hr.
3. Ramped to 125° C. at 2.5° C./hr.
4. Soaked at 125° C. for 1–48 hrs.
5. Cooled to ≦30° C.

The reaction product, which had an inherent viscosity below 0.5 when measured in chloroform at a concentration of 0.25 g/dl, was used as the coating composition in Examples 2 and 3 which follow.

EXAMPLE 2: COMPARATIVE EXAMPLES 1-3

Suture knot security for a coated suture in accordance with this invention (Example 2) and three known types of suture (Comparative Examples 1-3) was evaluated in divided canine fascia (linea alba) using a standard surgeon's knot.

The sutures of Example 2 were size 0 synthetic absorbable braided sutures constructed in accordance with U.S. Pat. No. 5,019,093, and coated with approximately 2.6 percent by weight of suture with the coating composition of Example 1 using the apparatus of Ser. No. 07/652,929, supra, by passing the suture through calender rolls, past a coating head to deposit the desired amount of coating composition in solvent and evaporating the solvent in a drying oven. Thereafter, the coated suture was calendered and filled with approximately 10 weight percent lycerin/calcium lactate in accordance with U.S. Pat. No. 5,037,429 using the calendering and filling apparatus of Ser. No. 07/652,939.

The sutures of Comparative Example 1 were size 0 Vicryl® synthetic absorbable braided sutures from Ethicon Inc. The sutures are believed to be coated with a copolymer of glycolide/lactide with calcium stearate.

The sutures of Comparative Example 2 were size 0 sutures constructed in accordance with U.S. Pat. No. 5,019,093, coated with approximately 1.4 percent by weight of suture with a 50:50 weight ratio copolymer of glycolide/lactide (18:82 mole percent) and poly(oxyethylene) glycol as disclosed in pending U.S. patent application Ser. No. 07/707,437, U.S. Pat. No. 5,123,912, referred to above and filled with approximately 10 weight percent glycerin/calcium lactate in accordance with U.S. Pat. No. 5,037,429. The sutures of Comparative Example 3 were coated and filled in substantially the same manner as in Example 2 employing the same equipment.

The sutures of Comparative Example 3 were the same as the sutures of Comparative Example 2 except that the coating was applied at approximately 3.0 percent by weight of suture.

The knot was configured as a hand tie (two right over left throws plus one left over right throw). The sutures were evaluated in normal abdominal fascia as well as thicker fascia toward the pubis The results of the testing are set forth below as the number of sutures which held without slipping per total number of sutures tied.

|  | Normal Fascia | Heavy Fascia |
| --- | --- | --- |
| Example 2 | 4:4 | 4:6 |
| Comparative Example 1 | 4:8 | 3:4 |
| Comparative Example 2 | 1:3 | 0:2 |
| Comparative Example 3 | 1:6 | — |

These results demonstrate the superior knot security characteristics conferred by the suture coating composition of this invention compared to that obtained with known coating compositions.

EXAMPLE 3; COMPARATIVE EXAMPLES 4–6

Knot run-down for a coated suture in accordance with this invention (Example 3) and three known types of suture (Comparative Examples 4-6) was evaluated by forming a hand tied square knot (right over left throw plus left over right throw) approximately 1 cm from the fascial edge of canine tissue and then running the knot down tightly around the fascial edge.

The sutures of Example 3 were size 3/0 sutures identical in all other respects to the sutures of Example 2 and the sutures of Comparative Examples 4, 5 and 6 were size 3/0 sutures identical in all other respects to the sutures of Comparative Examples 1, 2 and 3, respectively The results of the testing are set forth below as the number of sutures which ran down and the total number of tries.

|  | Knot Run Down |
| --- | --- |
| Example 3 | 4:6 |
| Comparative Example 4 | 6:6 |
| Comparative Example 5 | 3:6 |
| Comparative Example 6 | 2:6 |

The test results show that sutures coated with the coating composition of the present invention demonstrate superior run-down characteristics compared to sutures of identical construction which have been coated with the composition disclosed in pending U.S. patent application Ser. No. 07/707,437, filed May 28, 1991, referred to above. Moreover, the properties of the coated suture compare favorably with those of a commercial suture of comparable size.

What is claimed is:

1. A suture coated with a coating composition comprising the product obtained by reacting a mixture of poly(oxypropylene) glycol and lactide/glycolide copolymer.

2. The suture of claim 1 wherein the poly(oxypropylene) glycol possesses a molecular weight of from about 400 to about 6,000.

3. The suture of claim 1 wherein the poly(oxypropylene) glycol possesses a molecular weight of from about 1,000 to about 4,000.

4. The suture of claim 1 wherein the lactide/ glycolide copolymer is prepared with L-lactide.

5. The suture of claim 1 wherein the lactide/glycolide copolymer contains from about 90 to about 65 mole percent lactide and from about 10 to about 35 mole percent glycolide.

6. The suture of claim 1 wherein the lactide/glycolide copolymer contains from about 85 to about 70 mole percent lactide and from about 15 to about 30 mole percent glycolide.

7. The suture of claim 1 wherein the lactide/glycolide copolymer prior to reaction with the poly(oxypropylene) glycol possesses a glass transition temperature of at least about 54° C. when measured by differential scanning calorimetry at 20° C./min and an inherent viscosity of at least about 0.9 when measured in chloroform at a concentration of 0.25 g/dl.

8. The suture of claim 7 wherein the composition following reaction possesses an inherent viscosity of less than about 0.9 when measured in chloroform at a concentration of 0.25 g.dl.

9. The suture of claim 7 wherein the composition following reaction possesses an inherent viscosity of less than about 0.5 when measured in chloroform at a concentration of 0.25 g/dl.

10. The suture of claim 1 wherein the weight ratio of poly(oxypropylene) glycol to lactide/glycolide copolymer is from about 4:1 to about 1:4.

11. The suture of claim 1 wherein the weight ratio of poly(oxypropylene) glycol to lactide/glycolide copolymer is from about 2:1 to about 1:2.

12. The suture of claim 1 wherein the composition following reaction possesses in inherent viscosity of less than about 0.9 when measured in chloroform at a concentration of 0.25 g/dl.

13. The suture of claim 1 wherein the composition following reaction possesses an inherent viscosity of less than about 0.5 when measured in chloroform at a concentration of 0.25 g/dl.

14. The suture of claim 1 wherein the poly(oxypropylene) glycol is reacted with the lactide/glycolide copolymer in the presence of an initiator.

15. The suture of claim 14 wherein the initiator is a glycol.

16. The suture of claim 15 wherein the glycol is diethylene glycol.

17. The suture of claim 1 wherein the suture is a synthetic multifilament suture.

18. The suture of claim 1 wherein the suture is an absorbable synthetic multifilament suture.

19. The suture of claim 1 exhibiting improved knot tie-down and/or knot security characteristics compared with the knot tie-down and/or knot security characteristics of the same suture coated with an equivalent amount of an absorbable composition obtained by reacting a poly(oxyethylene) glycol with a mixture of lactide and glycolide and/or lactide/glycolide copolymer.

20. A method of improving the knot tie-down and/or knot security characteristics of a suture which comprises coating the suture with an absorbable composition comprising the product obtained by reacting a mixture of poly(oxypropylene) glycol and lactide/glycolide copolymer.

21. The method of claim 20 wherein the poly(oxypropylene) glycol possesses a molecular weight of from about 400 to about 6,000.

22. The method of claim 20 wherein the poly(oxypropylene) glycol possesses a molecular weight of from about 1,000 to about 4,000.

23. The method of claim 20 wherein the lactide/glycolide copolymer is prepared with L-lactide.

24. The method of claim 20 wherein the lactide/glycolide copolymer contains from about 90 to about 65 mole percent lactide and from about 10 to about 35 mole percent glycolide.

25. The method of claim 20 wherein the lactide/glycolide copolymer contains from about 85 to about 70 mole percent lactide and from about 15 to about 30 mole percent glycolide.

26. The method of claim 20 wherein the lactide/glycolide copolymer prior to reaction with the poly(oxypropylene) glycol possesses a glass transition temperature of at least about 54° C. when measured by differential scanning calorimetry at 20° C./min and an inherent viscosity of at least about 0.9 when measured in chloroform at a concentration of 0.25 g/dl.

27. The method of claim 26 wherein the composition following reaction possesses an inherent viscosity of less than about 0.9 when measured in chloroform at a concentration of 0.25 g.dl.

28. The method of claim 26 wherein the composition following reaction possesses an inherent viscosity of less than about 0.5 when measured in chloroform at a concentration of 0.25 g/dl.

29. The method of claim 20 wherein the weight ratio of poly(oxypropylene) glycol to lactide/glycolide copolymer is from about 4:1 to about 1:4.

30. The method of claim 20 wherein the weight ratio of poly(oxypropylene) glycol to lactide/glycolide copolymer is from about 2:1 to about 1:2.

31. The method of claim 20 wherein the poly(oxypropylene) glycol is reacted with the lactide/glycolide copolymer in the presence of an initiator.

32. The suture of claim 31 the initiator is a glycol.

33. The suture of claim 32 wherein the glycol is diethylene glycol.

34. The method of claim 20 wherein the suture is a synthetic multifilament suture.

35. The method of claim 20 wherein the suture is an absorbable synthetic multifilament suture.

36. The method of claim 20 wherein the resulting coated suture exhibits improved knot tie-down and/or knot security characteristics compared with the knot tie-down and/or knot security characteristics of the same suture coated with an equivalent amount of an absorbable composition obtained by reacting a poly(oxyethylene) glycol with a mixture of lactide and glycolide and/or lactide/glycolide copolymer.

* * * * *